(12) United States Patent
Storch et al.

(10) Patent No.: US 12,714,499 B2
(45) Date of Patent: Aug. 25, 2026

(54) DETERMINING A SURGICAL PORT FOR A TROCAR OR LAPAROSCOPE

(71) Applicant: Brainlab AG, Munich (DE)

(72) Inventors: Ferdinand Storch, Munich (DE); Mark Fingerle, Munich (DE); Martin Immerz, Munich (DE)

(73) Assignee: Brainlab AG, Munich (DE)

( * ) Notice: Subject to any disclaimer, the term of this patent is extended or adjusted under 35 U.S.C. 154(b) by 1133 days.

(21) Appl. No.: 17/598,107

(22) PCT Filed: Mar. 25, 2019

(86) PCT No.: PCT/EP2019/057424
§ 371 (c)(1),
(2) Date: Sep. 24, 2021

(87) PCT Pub. No.: WO2020/192883
PCT Pub. Date: Oct. 1, 2020

(65) Prior Publication Data

US 2022/0183759 A1 Jun. 16, 2022

(51) Int. Cl.
*A61B 34/10* (2016.01)
*A61B 34/20* (2016.01)
*A61B 34/30* (2016.01)

(52) U.S. Cl.
CPC .............. *A61B 34/10* (2016.02); *A61B 34/20* (2016.02); *A61B 34/30* (2016.02);
(Continued)

(58) Field of Classification Search
CPC ......... A61B 34/10; A61B 34/20; A61B 34/30; A61B 2034/102; A61B 2034/105; A61B 2034/107; A61B 2034/301
See application file for complete search history.

(56) References Cited

U.S. PATENT DOCUMENTS 11,779,412 B2 * 10/2023 Ida ......................... A61B 34/10 606/1
11,842,030 B2 * 12/2023 Koenig ............... G06F 3/04817
(Continued)

FOREIGN PATENT DOCUMENTS

WO WO-2008030263 A1 * 3/2008 ........... G06T 7/0012

OTHER PUBLICATIONS

Bauernschmitt, et al. Optimal Port Placement and Enhanced Guidance in Robotically Assisted Cardiac Surgery, dated Dec. 16, 2006, 4 pages.

(Continued)

*Primary Examiner* — Kibrom K Gebresilassie
(74) *Attorney, Agent, or Firm* — TUCKER ELLIS LLP

(57) ABSTRACT

Disclosed is a computer-implemented method of determining an entry region for inserting elongated medical instruments such as trocars or laparoscopes into an anatomical body part such as the abdomen. The determination is made on the basis of a patient image and a known or assumed geometry of the medical instruments and a known position of the target region, and risk structures which shall be avoided by the medical instrument are determined either by user interaction from the patient image or automatically by matching the patient image with an atlas defining the position of such risk structures in an image-based model of the anatomical body part. On the basis of the position of the determined entry region, a robotic device may be controlled to attain a position which is suitable for automatic insertion of the medical instruments into the anatomical body part.

19 Claims, 3 Drawing Sheets

(52) U.S. Cl.
CPC ... *A61B 2034/102* (2016.02); *A61B 2034/105* (2016.02); *A61B 2034/107* (2016.02); *A61B 2034/301* (2016.02)

(56) References Cited

U.S. PATENT DOCUMENTS

2016/0070436 A1* 3/2016 Thomas ................ G06T 7/0012
715/771
2016/0314710 A1* 10/2016 Jarc ...................... G09B 23/285
2020/0008874 A1* 1/2020 Barbagli ................ G16H 20/40

OTHER PUBLICATIONS

Hess, et al. Visual Design and Verification Tool for Collision-Free Dexterous Patient Specific Neurosurgical Instruments, 2016, 18 pages.
Paolis, et al. Advanced Interface for the Pre-Operative Planning and the Simulation of the Abdominal Access in Pediatric Laparoscopy, 2011, 10 pages.
Tobergte, et al. Planning and Control of a Teleoperational System for Research in Minimally Invasive Robotic Surgery, May 2009, 8 pages.

* cited by examiner

DETERMINING A SURGICAL PORT FOR A TROCAR OR LAPAROSCOPE

RELATED APPLICATION DATA

This application is a National Phase application of International Application No. PCT/EP2019/057424, filed Mar. 25, 2019, the contents of which are incorporated herein by reference.

FIELD OF THE INVENTION

The present invention relates to a computer-implemented method of planning an entry region for insertion of at least two medical instruments into an anatomical body part of a patient, a corresponding computer program, a program storage medium storing such a program and a computer for executing the program, as well as a medical system comprising an electronic data storage device and the aforementioned computer.

TECHNICAL BACKGROUND

Placement of a trocar for inserting a laparoscope is an essential part of a laparoscopic workflow (e.g. in visceral surgery, urology, gynecology). Approximately 50% of all complications in laparoscopy are related to the initial trocar placement. Trocar placement therefore directly influences the surgical outcome and in addition determines the ergonomics for the surgeon.

The inventors propose a technical solution to plan trocar positions pre-operatively, avoid anatomical risk structures, consider boundary conditions like instrument geometries, robot kinematics, personal preferences, visualize pre-planned trocars, and simplify the setup process for laparoscopic robotic systems Typically, trocars are placed by the surgeon who subsequently also performs the intervention. The positions are determined by a combination of anatomical knowledge, surgical guidelines, experience and personal preference. Approaches that use pre-operative anatomical scans and planning software for the determination of the trocar positions exist but have not become generally accepted and also differ from the approach described in this document.

The following issues had to be considered when making the present invention:

Trocar placement is highly dependent on skill and experience and is therefore error-prone.

Patient specific anatomical data from pre-operative scans is typically not considered.

The final entry positions greatly vary from surgeon to surgeon and patient to patient. Therefore, this task typically cannot be delegated to interns and therefore consumes valuable time of surgeons and chief surgeons.

The present invention has the object of providing an improved, for example more efficient and/or more reliable, method of planning an entry region for inserting a medical instrument such as a trocar or a laparoscope or other elongated rigid instrument.

The present invention can be used for procedures e.g. in connection with a navigation platform like Kick, Kick EM, Curve, or BUZZ or augmented reality devices provided for example by Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE INVENTION

In the following, a short description of the specific features of the present invention is given which shall not be understood to limit the invention only to the features or a combination of the features described in this section.

The disclosed method encompasses a workflow for determining an entry region for inserting elongated medical instruments such as laparoscopic instruments including trocars or laparoscopes into an anatomical body part such as the abdomen. The determination is made on the basis of a patient image and a known or assumed geometry of the medical instruments and a known position of the target region, and risk structures which shall be avoided by the medical instrument are determined either by user interaction from the patient image or automatically by matching the patient image with an atlas defining the position of such risk structures in an image-based model of the anatomical body part. On the basis of the position of the determined entry region, a robotic device may be controlled to attain a position which is suitable for automatic insertion of the medical instruments into the anatomical body part.

GENERAL DESCRIPTION OF THE INVENTION

In this section, a description of the general features of the present invention is given for example by referring to possible embodiments of the invention.

In general, the invention reaches the afore-mentioned object by providing, in a first aspect, a computer-implemented medical method of planning an entry region (i.e. a surgical port) for insertion of at least two medical instruments into an anatomical body part of a patient. The medical instruments are for example of elongate shape and in an example are trocars, laparoscopes or any other substantially rigid elongated instrument. A laparoscope is in this sense considered to be a substantially rigid elongated instrument because of the corresponding properties of its shaft, even though the tip of a laparoscope may be deflectable. The method according to the first aspect comprises executing, on at least one processor of at least one computer (for example at least one computer being part of a navigation system), the following exemplary steps which are executed by the at least one processor.

In a (for example first) exemplary step, patient image data is acquired which describes a (for example three-dimensional) medical patient image of at least a part of the patient's body including a surface of the anatomical body part. The anatomical body part comprises for example at least part of the abdomen or at least part of the skull and brain or an organ in the pelvic cavity (such as reproductive organs, the urinary bladder, the pelvic colon, the rectum, the vagina, or the uterus) or an organ in the thoracic cavity (such as the heart, the thoracic aorta, the pulmonary artery and/or all its branches, the diaphragm, the trachea, the bronchi and the lungs). The patient image data has been generated by applying a medical imaging modality to the anatomical body part such as a tomographic imaging modality which produces three-dimensional image data, for example magnetic resonance imaging or computed x-ray tomography.

In a (for example second) exemplary step, target region data is acquired which describes the position of a target region in the patient's body, wherein the target region defines a region in the patient's body which is to be treated by using the medical instrument. In an example, the target region is part of the anatomical body part and for example comprises at least part of the abdomen or at least part of the brain.

In a (for example third) exemplary step, instrument geometry data is acquired which describes at least one geometric design parameter for each of the medical instruments. In one example, the geometric design parameter is the length of each of the medical instruments. The geometric design parameter is for example defined as a standard value which is usually applied to define the geometry of the relevant type of medical instrument such as an average length between the handle and the tip of the laparoscope.

In a (for example fourth) exemplary step, entry region data is determined based on the patient image data and the target region data and the instrument geometry data, wherein the entry region geometry data describes a shape and position of the entry region. The entry region is a region on the surface of the anatomical body part described by the medical patient image. At least the shape of the entry region is determined in dependence on the geometry (e.g. the shape and position) of target region and geometric design parameter in consideration of risk structures. The term of shape includes the meaning of contour, e.g. a contour of the entry region and of the target region in a two-dimensional projection, for example along the insertion directions along which the medical instruments shall be inserted into the anatomical body part. The medical instruments are for example rigid so that they can be inserted only along a linear (i.e. straight) path. For example, the entry region has a finite extent and comprises a plurality, for example a multitude, of points. The entry region may be a single region or different regions. For example, the entry region consists of a (for example single) coherent region of the surface of the anatomical body part or comprises a plurality of disjunct regions of the surface of the anatomical body part. In one example, the entry region lies in a region of the surface of the anatomical body part which has been selected by a user.

In a further exemplary step, atlas data is acquired which describes an image-based model of the at least part of the patient's body including a description of the position of at least one avoidance region, wherein the entry region data is determined further based on the atlas data. The term of avoidance region defines a region in the anatomical body part which shall not be traversed or otherwise influenced in an undesired manner by the medical instruments when they are inserted into the anatomical body part. In that sense, an avoidance region may comprise or consist of an organ-at-risk (i.e. a risk structure) which shall not be traversed or otherwise be influenced by the medical instruments when they are inserted. Alternatively or additionally, the at least one avoidance region is determined, for example marked, for example manually or semi-automatically.

If atlas data is available it could be combined with information from an HIS (Hospital Information System) concerning the type of target region for a fully automatic definition of the target region by segmenting it from the medical patient image using the atlas data as a comparison for the segmentation. Alternatively or additionally, the target region is determined, for example marked, for example manually or semi-automatically.

In a further exemplary step, insertion angle data is acquired which describes at least one of an angle between the surface of the anatomical body part and a longitudinal dimension of the medical instrument at which the medical instrument shall be inserted into the anatomical body part, or an orientation in space at which the medical instrument shall be inserted into the anatomical body part, wherein the entry region data is determined further based on the insertion angle data.

Considering the aforementioned angle or orientation, respectively, enhances the ergonomy of using the medical instruments by allowing a working position which is favourable for the user's ergonomy.

In a further exemplary step, working space data is determined based on the instrument geometry data and the target region data and the entry region data. The working space data describes a working space of each of the medical instruments which is required for using the medical instruments for treating the target region, wherein the entry region data is determined further based on the working space data. The working space is defined for example by the freedom of movement required by the medical instruments for properly using the medical instruments and defined by a movement area in which the medical instruments needs to be moved for using it as desired, including the freedom of movement of an entity moving the medical instruments such as an arm of a robotic device or a user's arm defined by the area in which that entity needs to be moved for using the associated medical instrument as desired. For example, the entry region data is determined under the condition that the working spaces of the at least two medical instruments do not touch each other outside the anatomical body part and/or do not overlap outside the anatomical body part. For example, each of the working spaces is at least substantially cone-shaped with the apex of the cones, respectively, positioned in the entry region, for example on the area on the surface of the anatomical body part defining the entry region. For example, the working spaces are all defined to lie entirely outside the patient's body.

In a second aspect, the invention is directed to a method for determining control data for controlling the position of at least one end effector of at least one robotic device, comprising the following steps:

a) the method according to the first aspect is executed; and
b) control data is determined based on the entry region data, wherein the control data describes at least one command to be issued to the robotic device for positioning the at least one end effector to allow for introduction of at least one of the at least two medical instruments into the anatomical body part in accordance with the entry region data and, as far the method according to the first aspect comprises acquiring the insertion angle data, the insertion angle data.

In a third aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect. The invention may alternatively or additionally relate to a (physical, for example electrical, for example technically generated) signal wave, for example a digital signal wave, such as an electromagnetic carrier wave carrying information which represents the program, for example the aforementioned program, which for example comprises code means which are adapted to perform any or all of the steps of the method according to the first aspect. A computer program stored on a disc is a data file, and when the file is read out and transmitted it becomes a data stream for example in the form of a (physical, for example electrical, for example technically generated) signal. The signal can be implemented as the signal wave, for example as the electromagnetic carrier wave which is described herein. For example, the signal, for example the signal wave is constituted to be transmitted via a computer network, for example LAN, WLAN, WAN, mobile network, for example the internet. For example, the signal, for example the signal wave, is constituted to be transmitted by optic or acoustic data transmission. The invention according to the third aspect therefore may alternatively or additionally relate to a data stream representative of the aforementioned program.

In a fourth aspect, the invention is directed to a computer-readable program storage medium on which the program according to the third aspect is stored. The program storage medium is for example non-transitory.

In a fifth aspect, the invention is directed to at least one computer (for example, a computer), comprising at least one processor (for example, a processor) and at least one memory (for example, a memory), wherein the program according to the third aspect is running on the processor or is loaded into the memory, or wherein the at least one computer comprises the computer-readable program storage medium according to the third aspect.

In a sixth aspect, the invention is directed to a medical system, comprising:

a) the at least one computer according to the fifth aspect;

a) at least one electronic data storage device storing at least the entry region data; and b) a robotic device for inserting at least one of the at least two medical devices into the anatomical body part, wherein the at least one computer is operably coupled to the at least one electronic data storage device for acquiring, from the at least one data storage device, at least the entry region data, and the robotic device for issuing a control signal to the robotic device for controlling the operation of the robotic device on the basis of the entry region data and, as far the program running on the computer or loaded into the memory of the computer causes the computer to acquire the insertion angle data, the insertion angle data.

In a seventh aspect, the invention is directed to use of the method according to the first or second aspect for planning a surgical procedure (e.g. laparoscopy), wherein the use comprises execution of the steps of the method according to the first or second aspect for planning the surgical procedure.

For example, the invention does not involve or in particular comprise or encompass an invasive step which would represent a substantial physical interference with the body requiring professional medical expertise to be carried out and entailing a substantial health risk even when carried out with the required professional care and expertise.

For example, the invention does not comprise a step of inserting the medical instruments in the anatomical body part. More particularly, the invention does not involve or in particular comprise or encompass any surgical or therapeutic activity. The invention is instead directed as applicable to planning a surgical procedure. For this reason alone, no surgical or therapeutic activity and in particular no surgical or therapeutic step is necessitated or implied by carrying out the invention.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term computer includes a server resource. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (VVWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, such as an electromagnetic carrier wave carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing (and e.g. outputting) the data by means of a computer and for example within the framework of the method in accordance with the invention. A step of "determining" as described herein for example comprises or consists of issuing a command to perform the determination described herein. For example, the step comprises or consists of issuing a command to cause a computer, for example a remote computer, for example a remote server, for example in the cloud, to perform the determination. Alternatively or additionally, a step of "determination" as described herein for example comprises or consists of receiving the data resulting from the determination described herein, for example receiving the resulting data from the remote computer, for example from that remote computer which has been caused to perform the determination. The meaning of "acquiring data" also for example encompasses the scenario in which the data are received or retrieved by (e.g. input to) the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) ora local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises image information (for example, positional image information) which can be matched (for example by applying an elastic or rigid image fusion algorithm) for example to image information (for example, positional image information) contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

For example, the atlas data includes information of the anatomical body part. This information is for example at least one of patient-specific, non-patient-specific, indication-specific or non-indication-specific. The atlas data therefore describes for example at least one of a patient-specific, non-patient-specific, indication-specific or non-indication-specific atlas. For example, the atlas data includes movement information indicating a degree of freedom of movement of the anatomical body part with respect to a given reference (e.g. another anatomical body part). For example, the atlas is a multimodal atlas which defines atlas information for a plurality of (i.e. at least two) imaging modalities and contains a mapping between the atlas information in different imaging modalities (for example, a mapping between all of the modalities) so that the atlas can be used for transforming medical image information from its image depiction in a first imaging modality into its image depiction in a second imaging modality which is different from the first imaging modality or to compare (for example, match or register) images of different imaging modality with one another.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Mapping describes a transformation (for example, linear transformation) of an element (for example, a pixel or voxel), for example the position of an element, of a first data set in a first coordinate system to an element (for example, a pixel or voxel), for example the position of an element, of a second data set in a second coordinate system (which may have a basis which is different from the basis of the first coordinate system). In one embodiment, the mapping is determined by comparing (for example, matching) the color values (for example grey values) of the respective elements by means of an elastic or rigid fusion algorithm. The mapping is embodied for example by a transformation matrix (such as a matrix defining an affine transformation).

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

The n-dimensional image of a body is registered when the spatial location of each point of an actual object within a space, for example a body part in an operating theatre, is assigned an image data point of an image (CT, MR, etc.) stored in a navigation system.

BRIEF DESCRIPTION OF THE DRAWINGS

In the following, the invention is described with reference to the appended figures which give background explanations and represent specific embodiments of the invention. The scope of the invention is however not limited to the specific features disclosed in the context of the figures, wherein.

DESCRIPTION OF EMBODIMENTS

Figure 1:
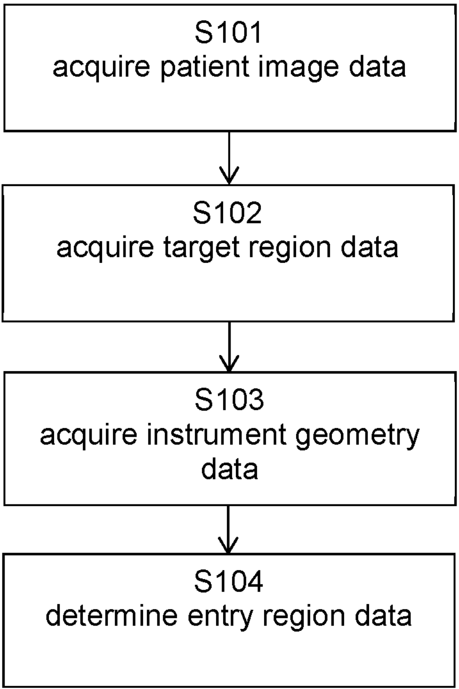
FIG. 1 illustrates a basic flow of the method according to the first aspect.

FIG. 1 illustrates the basic steps of the method according to the first aspect, in which step S101 encompasses acquisition of the patient image data, step S102 encompasses acquisition of the target region data and subsequent step S103 encompasses acquisition of the instrument geometry data. On the basis of the data acquired in those steps, the entry region data is determined in step S104.

Figure 2:
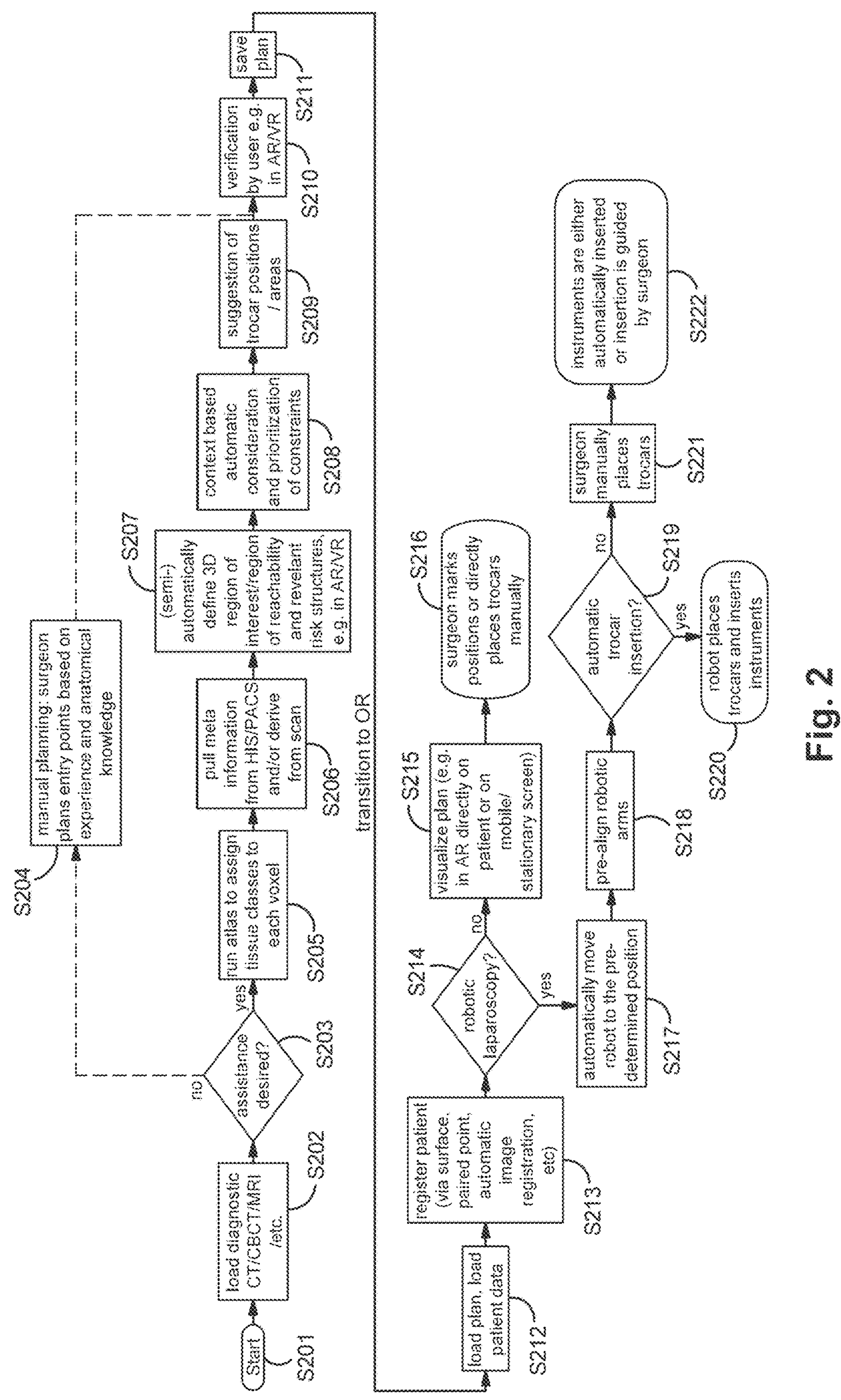
FIG. 2 shows an example of the method according to the first aspect.

FIG. 2 describes a specific example of the method according to the first aspect. In step S201, execution of the method is started for example by calling an executable file. In step S202, the patient image data is acquired by loading a CT (computed x-ray tomography), CBCT (cone beam computed tomography) or MRI (magnetic resonance image) or another tomographic image. The method then continues with asking a user in step S203 whether he or she desires assistance, If no assistance is desired, the method carries on with executing step S204 in which the surgeon is offered the possibility of planning the entry regions manually based on his or her experience and anatomical knowledge, which is then followed by step S210. If step S203 reveals that assistance is desired, the method continues with step S205 encompassing running an atlas, i.e. fusing it with the medical patient image to segment, in the patient medical image, structures corresponding to risk structures defined in the atlas. In subsequent step S206, meta information about the surgical procedure envisaged to be carried out on the patient is pulled from a hospital information system or picture archiving and communication system (PACS) and/or is additionally derived from the scan (i.e. the medical patient image). In the following step S207, the region of interest and/or the region of reachability (i.e. which can be reached by the medical instruments assuming a specific entry region) and the positions of relevant risk structures are automatically or semi-automatically defined. This may be done for example in AR (augmented reality) or VR (virtual reality), for example by displaying the result on a corresponding device worn by the surgeon so that he can view the result in relation to the patient's body. In step S208, a context-based automatic consideration and prioritization of constraints is then executed, followed by outputting, in step S209, a suggestion of positions or areas for placing a trocar used for inserting the medical instrument (e.g. the laparoscope), i.e. for the entry region. The user can then verify the result in AR or VR. The resulting plan for conducting the surgical procedure is then saved in step S211. The patient is then transferred to the OR (operating room), where the plan is loaded in together with the patient data in step S212. Then, step S213 is executed which encompasses registering the patient to the coordinate system used for navigating the surgical procedure, for example by surface paired point registration, automatic image registration or a comparable approach. Step S214 then determines whether robotic laparoscopy is envisaged as the surgical procedure. If this is answered in the positive, the method continues with step S217 by determining the control data for controlling the position of an end effector of the robotic device and issuing a control signal, i.e. a command, to the robotic device for moving the end effector to a predetermined position, followed by step S218 encompassing pre-alignment of the arm of the robotic device with a position suitable for inserting the trocar. Then, the method asks the user in step S219 whether the trocar shall be inserted automatically. If this is answered in the positive, the robotic device places the trocar and inserts the medical instruments in step S220. If step S219 is answered in the negative, the surgeon manually places the trocar in step S221 which is followed by step S222 encompassing either automatic insertion or surgeon-guided insertion of the medical instruments. If step S214 is answered in the negative, the method enters step S215 in which the plan for the surgical procedure is visualized, for example in AR, displaying the entry region directly on the surface of the patient's body or on a mobile or stationary screen, after which the surgeon marks the position of the entry region on the patient's body or directly places the trocars manually in step S216.

Figure 3:
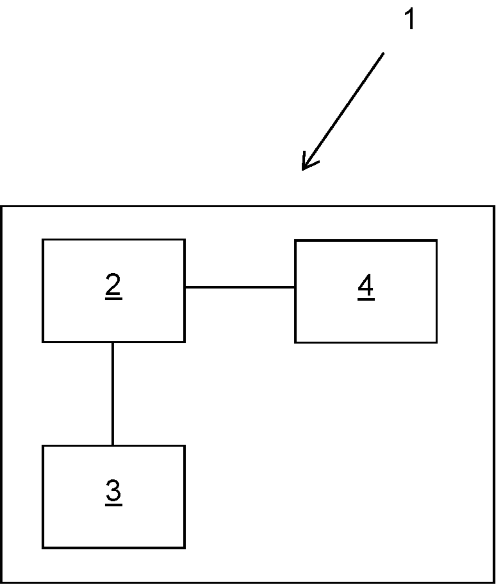
FIG. 3 is a schematic illustration of the system according to the sixth aspect.

FIG. 3 is a schematic illustration of the medical system 1 according to the sixth aspect. The system is in its entirety identified by reference sign 1 and comprises a computer 2, an electronic data storage device (such as a hard disc) 3 for storing at least the entry region data and a robotic device 4 (such as a mechatronic articulable arm). The components of the medical system 1 have the functionalities and properties explained above with regard to the sixth aspect of this disclosure.

The invention claimed is:

1. A computer-implemented method in a medical procedure planning system including a computer system having a processor and a non-transitory memory device operatively coupled with the processor for planning an entry region for an insertion of at least two medical instruments into an anatomical body part of a patient, the method comprising:

acquiring, by the processor of the computer system, patient image data that describes a medical patient image of at least a part of the patient's body including a surface of the anatomical body part;

acquiring, by the processor of the computer system, target region data that describes a position and a geometry of a target region in the patient's body, wherein the target region defines a region in the patient's body that is to be treated by using the at least two medical instruments;

acquiring, by the processor of the computer system, instrument geometry data that describes at least one geometric design parameter for each of the at least two medical instruments;

automatically determining, by the processor of the computer system, entry region data based on the patient image data, the position and geometry of the target region, and the instrument geometry data, wherein the entry region data describes a shape and position of an insertion area on the surface of the anatomical body part of the patient defining the entry region for receiving the insertion of the at least two medical instruments into the anatomical body part of the patient for treating the target region in the patient's body using the at least two medical instruments; and automatically determining, by the processor of the computer system, a contour of the entry region based on: i) a contour of the target region, and ii) positions of one or more risk structures to be avoided by the at least two medical instruments, wherein the entry region is defined as: i) a single coherent region of the insertion area on the surface of the anatomical body part of the patient described by the medical patient image, the single coherent region of the insertion area having a finite extent defined by a plurality of spaced apart medical treatment instrument insertion points or ii) a plurality of distinct regions of the insertion area on the surface of the anatomical body part of the patient described by the medical patient image, each of the plurality of distinct regions having finite extents defined by a plurality of spaced apart medical treatment instrument insertion points.

2. The method according to claim 1, further comprising:

acquiring atlas data which describes an image-based model of the at least part of the patient's body including a description of the position of at least one avoidance region, wherein the determining the entry region data comprises determining the entry region data based on the atlas data.

3. The method according to claim 1, wherein:

the geometric design parameter describes a length of each of the medical instruments.

4. The method according to claim 1, wherein:

the entry region consists of a coherent region of the surface of the anatomical body part or wherein the entry region comprises a plurality of disjunct regions of the surface of the anatomical body part.

5. The method according to claim 1, further comprising:

acquiring insertion angle data which describes at least one of:

an angle between the surface of the anatomical body part and a longitudinal dimension of the medical instrument at which the medical instrument shall be inserted into the anatomical body part, and/or an orientation in space at which the medical instrument is to be inserted into the anatomical body part, wherein the entry region data is determined based on the insertion angle data.

6. The method according to claim 1, wherein:

the entry region lies in a region of the surface of the anatomical body part that has been selected by a user.

7. The method according to claim 1, further comprising:

determining working space data based on the instrument geometry data, the target region data, and the entry region data, wherein the working space data describes a working space of each of the medical instruments that is required for using the medical instruments for treating the target region, wherein the entry region data is determined further based on the working space data.

8. The method according to claim 1, wherein the automatically determining, by the processor of the computer system, the contour of the entry region comprises:

automatically determining, by the processor of the computer system, the contour of the entry region in a two-dimensional projection comprising insertion directions along which the at least two medical instruments are planned for the insertion into the anatomical body part of a patient while also avoiding the one or more risk structures.

9. The method according to claim 7, wherein:

the determining the entry region data comprises determining the entry data under a condition that the working spaces of the at least two medical instruments:

do not touch each other outside the anatomical body part; and/or do not overlap outside the anatomical body part.

10. The method according to claim 9, wherein each of the working spaces of the at least two medical instruments is cone-shaped with its apex positioned in the entry region.

11. The method according to claim 7, wherein the working spaces are all defined to lie entirely inside the patient's body or entirely outside the patient's body.

12. A method in a medical procedure planning system including a computer having a processor and a non-transitory memory device operatively coupled with the processor for determining control data for controlling the position of at least one end effector of at least one robotic device, comprising:

acquiring, by the processor of the computer system, patient image data that describes a medical patient image of at least a part of the patient's body including a surface of the anatomical body part;

acquiring, by the processor of the computer system, target region data that describes position and a geometry of a target region in the patient's body, wherein the target region defines a region in the patient's body that is to be treated by using the at least two medical instruments;

acquiring, by the processor of the computer system, instrument geometry data that describes at least one geometric design parameter for each of the at least two medical instruments;

automatically determining, by the processor of the computer system, entry region data based on the patient image data, the position and geometry of the target region, and the instrument geometry data, wherein the entry region data describes a shape and position of an insertion area on the surface of the anatomical body part of the patient defining an entry region for receiving the insertion of the at least two medical instruments into the anatomical body part of the patient for treating the target region in the patient's body using the at least two medical instruments, wherein the entry region is defined as:

i) a single coherent region of the insertion area on the surface of the anatomical body part of the patient described by the medical patient image, the single coherent region of the insertion area having a finite extent defined by a plurality of spaced apart medical treatment instrument insertion points, or ii) a plurality of distinct regions of the insertion area on the surface of the anatomical body part of the patient described by the medical patient image, each of the plurality of distinct regions having finite extents defined by a plurality of spaced apart medical treatment instrument insertion points;

automatically determining, by the processor of the computer system, a contour of the entry region based on: i) a contour of the target region, and ii) positions of one or more risk structures to be avoided by the at least two medical instruments; and automatically determining, by the processor of the computer system, control data based on the entry region data, wherein the control data describes at least one command to be issued to the robotic device for positioning the at least one end effector to allow for introduction of at least one of the at least two medical instruments into the anatomical body part in accordance with the entry region data.

13. The method according to claim 12, further comprising:

acquiring insertion angle data which describes at least one of:

an angle between the surface of the anatomical body part and a longitudinal dimension of the medical instrument at which the medical instrument shall be inserted along an insertion direction into the anatomical body part, and/or an orientation in space at which the medical instrument is to be inserted into the anatomical body part along the insertion direction, wherein the determining the control data describing the at least one command to be issued to the robotic device for positioning the at least one end effector comprises:

determining the control data based on the entry region and insertion angle data.

14. The method according to claim 13, wherein the automatically determining, by the processor of the computer system, the contour of the entry region comprises:

automatically determining, by the processor of the computer system, the contour of the entry region in a two-dimensional projection comprising plural insertion directions along which the at least two medical instruments are planned for the insertion into the anatomical body part of a patient while also avoiding the one or more risk structures.

15. A non-transient memory device storing program logic thereon that when the program logic is executed by a processor device of a computer causes the computer to perform a computer-implemented medical method of planning an entry region for an insertion of at least two medical instruments into an anatomical body part of a patient, the method comprising:

acquiring patient image data at the processor device of the computer, wherein the patient image data describes a medical patient image of at least a part of the patient's body including a surface of the anatomical body part;

acquiring target region data at the processor device of the computer, wherein the target region data describes a position and a geometry of a target region in the patient's body, wherein the target region defines a region in the patient's body that is to be treated by using the at least two medical instruments;

acquiring instrument geometry data at the processor device of the computer, wherein the instrument geometry data describes at least one geometric design parameter for each of the at least two medical instruments; and automatically determining by the processor device of the computer entry region data based on the patient image data, the position and geometry of the target region, and the instrument geometry data, wherein the entry region data describes a shape and position of an insertion area on the surface of the anatomical body part of the patient defining the entry region for receiving the insertion of the at least two medical instruments into the anatomical body part of the patient for treating the target region in the patient's body using the at least two medical instruments;

automatically determining, by the processor of the computer system, a contour of the entry region based on: i) a contour of the target region, and ii) positions of one or more risk structures to be avoided by the at least two medical instruments, wherein the entry region is defined as: i) a single coherent region of the insertion area on the surface of the anatomical body part of the patient described by the medical patient image, the single coherent region of the insertion area having a finite extent defined by a plurality of spaced apart medical treatment instrument insertion points, or ii) a plurality of distinct regions of the insertion area on the surface of the anatomical body part of the patient described by the medical patient image, each of the plurality of distinct regions having finite extents defined by a plurality of spaced apart medical treatment instrument insertion points.

16. A medical system for planning an entry region for an insertion of at least two medical devices into an anatomical body part of a patient, the medical system comprising:

at least one computer comprising a processor device;

at least one electronic data storage device storing entry region data and target region data representative of a geometry of a target region in an associated patient; and a robotic device operable to insert at least one of the at least two medical devices into the anatomical body part of the associated patient, wherein the at least one computer is operably coupled with:

the at least one electronic data storage device for:

acquiring, from the at least one data storage device, at least the entry and target region data;

determining, by the processor device of the computer system, a contour of an entry region based on: i) a contour of the target region, and ii) positions of one or more risk structures to be avoided by the at least two medical instruments wherein the entry region is defined as: i) a single coherent region of the surface of the anatomical body part described by the medical patient image, the single coherent region having a finite extent defined by a plurality of spaced apart medical treatment instrument insertion points, or ii) a plurality of distinct regions of the surface of the anatomical body part described by the medical patient image, each of the plurality of distinct regions having finite extents defined by a plurality of spaced apart medical treatment instrument insertion points; and the robotic device for issuing a control signal to the robotic device for controlling operation of the robotic device based on the entry and target region data.

17. The medical system according to claim 16, wherein:

the at least one computer is operable to execute logic stored in the at least one electronic data storage device to perform a method comprising:

acquiring patient image data that describes a medical patient image of at least a part of the patient's body including a surface of the anatomical body part;

acquiring target region data that describes the position of a target region in the patient's body, wherein the target region defines a region in the patient's body that is to be treated by using the at least two medical instruments;

acquiring instrument geometry data that describes at least one geometric design parameter for each of the at least two medical instruments;

determining the entry region data based on the patient image data, the target region data, and the instrument geometry data, wherein the entry region data describes a shape and position of the entry region, wherein the entry region comprises a region on the surface of the anatomical body part described by the medical patient image.

18. The medical system according to claim 16, wherein the determining the contour of the entry region by the processor of the computer system comprises:

automatically determining the contour of the entry region in a two-dimensional projection comprising insertion directions along which the at least two medical instruments are planned for the insertion into the anatomical body part of a patient while also avoiding the one or more risk structures.

19. The medical system according to claim 17, wherein:

the at least one computer is operable to execute the logic stored in the at least one electronic data storage device to:

acquire insertion angle data that describes at least one of:

an angle between the surface of the anatomical body part and a longitudinal dimension of the medical instrument at which the medical instrument is to be inserted into the anatomical body part, and/or an orientation in space at which the medical instrument is to be inserted into the anatomical body part, wherein the at least one computer is operably coupled with the robotic device for issuing the control signal to the robotic device for controlling the operation of the robotic device based on the entry region and insertion angle data.

* * * * *